US012029880B2

(12) United States Patent
Sonderegger

(10) Patent No.: US 12,029,880 B2
(45) Date of Patent: Jul. 9, 2024

(54) NEEDLE HUB

(71) Applicant: Becton, Dickinson and Company, Franklin Lakes, NJ (US)

(72) Inventor: Ralph Sonderegger, Farmington, UT (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 99 days.

(21) Appl. No.: 17/586,914

(22) Filed: Jan. 28, 2022

(65) Prior Publication Data

US 2023/0241311 A1    Aug. 3, 2023

(51) Int. Cl.
*A61M 5/158* (2006.01)

(52) U.S. Cl.
CPC ..... *A61M 5/158* (2013.01); *A61M 2005/1585* (2013.01); *A61M 2005/1586* (2013.01)

(58) Field of Classification Search
CPC .......... A61M 5/158; A61M 2005/1585; A61M 2005/1586; A61M 2005/1583; A61M 2005/1587; A61M 5/162; A61M 5/1626; A61M 5/3202; A61M 25/0631; A61M 25/0618; A61M 25/0625; A61M 5/3216; A61M 2005/3217; A61M 2005/1581; A61M 5/32; A61M 5/3205; A61M 5/321; A61M 25/0612; A61M 39/20; A61M 5/3293; A61B 5/150374; A61B 5/150534; A61B 5/150664
See application file for complete search history.

(56) References Cited

U.S. PATENT DOCUMENTS

| | | | |
|---|---|---|---|
| 5,584,816 A * | 12/1996 | Gyure | A61M 5/3216 128/919 |
| 10,112,006 B2 | 10/2018 | Sonderegger et al. | |
| 2012/0029483 A1 | 2/2012 | Griffith et al. | |
| 2019/0192771 A1 * | 6/2019 | Sonderegger | A61M 5/158 |

* cited by examiner

*Primary Examiner* — Kami A Bosworth
*Assistant Examiner* — Avery Smale
(74) *Attorney, Agent, or Firm* — Dickinson Wright PLLC

(57) ABSTRACT

A needle hub including a core mounting structure, a first panel and a second panel each connected to the core mounting structure with an opening formed between the first panel and the second panel, and an introducer needle fixedly attached to the core mounting structure; a first actuation lever disposed within the opening, cantilevered at a central portion thereof from the core mounting structure that has a first actuation button disposed at a proximal free end and a first needle hub latch disposed at a distal free end. A needle tip shield is rotatably connected to one of the first panel and the second panel and rotatable from a first position in which a distal end of the introducer needle is exposed to a second position shielding the distal end of the introducer needle.

20 Claims, 14 Drawing Sheets

NEEDLE HUB

FIELD OF THE INVENTION

The present invention relates generally to needle hubs, and more particularly, to introducer needle hubs for use with infusion devices, such as subcutaneous infusion devices used in conjunction with an infusion pump in the infusion of insulin and other medicaments.

BACKGROUND OF THE INVENTION

One mode of insulin infusion treatment for diabetes includes infusion pump therapy via a catheter, needle or other type of cannula. Infusion pumps offer the advantages of continuous infusion of insulin, precision dosing, and programmable delivery schedules. Together, these advantages result in more accurate blood glucose control. In this mode of insulin infusion treatment, the infusion pump remains attached to the user and required doses of insulin are delivered to the user via the pump.

One type of cannula is a catheter, which generally is a tube that can be inserted into the body to permit the administration of fluids. In infusion pump therapy, the types and sizes of the catheter may vary, but generally, the catheter is a thin, flexible tube. In some uses, however, it may be larger and/or rigid.

One type of conventional infusion set is sold as the Quick-Set® infusion set by Medtronic. In such devices, the infusion pump includes a catheter assembly connected to a pump via a tubing set, and a separate insertion device inserts and/or attaches the catheter assembly into to a user via an introducer needle provided as part of the infusion set. The infusion set and insertion device can also be combined, as in the Mio® infusion set sold by Medtronic, which is an "all-in-one" design that combines the infusion set and insertion device into one unit.

A conventional infusion device can include a fluid connector hub, which may be releasably attached to a base that can be secured to a user's skin. An infusion pump supplies fluid to a catheter via the fluid connector hub/base engagement.

With conventional infusion devices, however, there are concerns that before and during insertion of the catheter, the introducer needle and catheter may move relative to one another. There is an axial relationship between the tip of the needle and the catheter, which is commonly known as the lie distance. The lie distance is ideally maintained within a suitable range during insertion of the catheter into a user when using the tip of the needle to puncture the skin, and is also ideally maintained within a suitable range as the shank of the needle carries the catheter into the subcutaneous region.

A suitable lie distance, however, sometimes cannot be maintained because of relative movement between the introducer needle and the catheter. If the lie distance is not suitable, the piercing resistance increases and can cause significant pain for a patient.

Additionally, after withdrawal of the introducer needle, it is desirable to shield introducer needle to prevent needle stick injuries.

As such, it may be appreciated that there is a continuing need for a new and improved needle hub for an introducer needle that addresses the problems noted above and is simple and low-cost to manufacture. Embodiments of the present invention substantially fulfill this need.

SUMMARY OF EMBODIMENTS OF THE INVENTION

Accordingly, it is an aspect of the present invention to provide a needle hub with a needle shield. It is another aspect of the present invention to provide a needle hub that can maintain a suitable lie distance.

The foregoing and/or other aspects of the present invention are achieved by providing a needle hub including a core mounting structure, first and second panels, each connected to the core mounting structure with an opening formed between the first panel and the second panel. An introducer needle fixedly attached to the core mounting structure for insertion into a patient. The needle hub further includes a first actuation lever disposed within the opening, cantilevered at a central portion thereof from the core mounting structure that has a first actuation button disposed at a proximal free end of the first actuation lever and a first needle hub latch disposed at a distal free end of the first actuation lever. A needle tip shield is rotatably connected to one of the first and second panels and is rotatable by a user from a first position in which a distal end of the introducer needle is exposed to a second position shielding the distal end of the introducer needle.

The foregoing and/or other aspects of the present invention are also achieved by providing a needle hub including a core mounting structure connected to an introducer needle. The needle hub includes a pair of actuation levers pivotally connected to the core mounting structure, each actuation lever comprising an actuation button disposed at a proximal cantilevered end and a needle hub latch disposed at a distal cantilevered end. The needle hub further includes a first panel connected to the core mounting structure and disposed adjacent to the pair of actuation levers and a needle tip shield rotatably connected to the first panel, and rotatable by a user from a first position in which a distal end of the introducer needle is exposed to a second position shielding the distal end of the introducer needle.

The foregoing and/or other aspects of the present invention are also achieved by providing a method, including inwardly pinching a proximal cantilevered end of a pivotally connected actuation lever of a needle hub having an introducer needle to outwardly displace a needle hub latch disposed on a distal cantilevered end of the pivotally connected actuation lever and unlatch the needle hub from a medicament device base. The method further includes proximally displacing the needle hub to remove the introducer needle from the medicament device base. The method further includes folding a rotatably connected needle tip shield of the needle hub from a first position in which a distal end of the introducer needle is exposed to a second position shielding the distal end of the introducer needle, and during such folding, causing the rotatably connected needle tip shield to contact and pivot the distal cantilevered end of the pivotally connected actuation lever inwardly.

Additional and/or other aspects and advantages of the present invention will be set forth in the description that follows, or will be apparent from the description, or may be learned by practice of the invention.

BRIEF DESCRIPTION OF THE DRAWINGS

The above and/or other aspects and advantages of embodiments of the invention will be more readily appreciated from the following detailed description, taken in conjunction with the accompanying drawings, of which.

DETAILED DESCRIPTION OF EMBODIMENTS OF THE PRESENT INVENTION

Figure 1A:
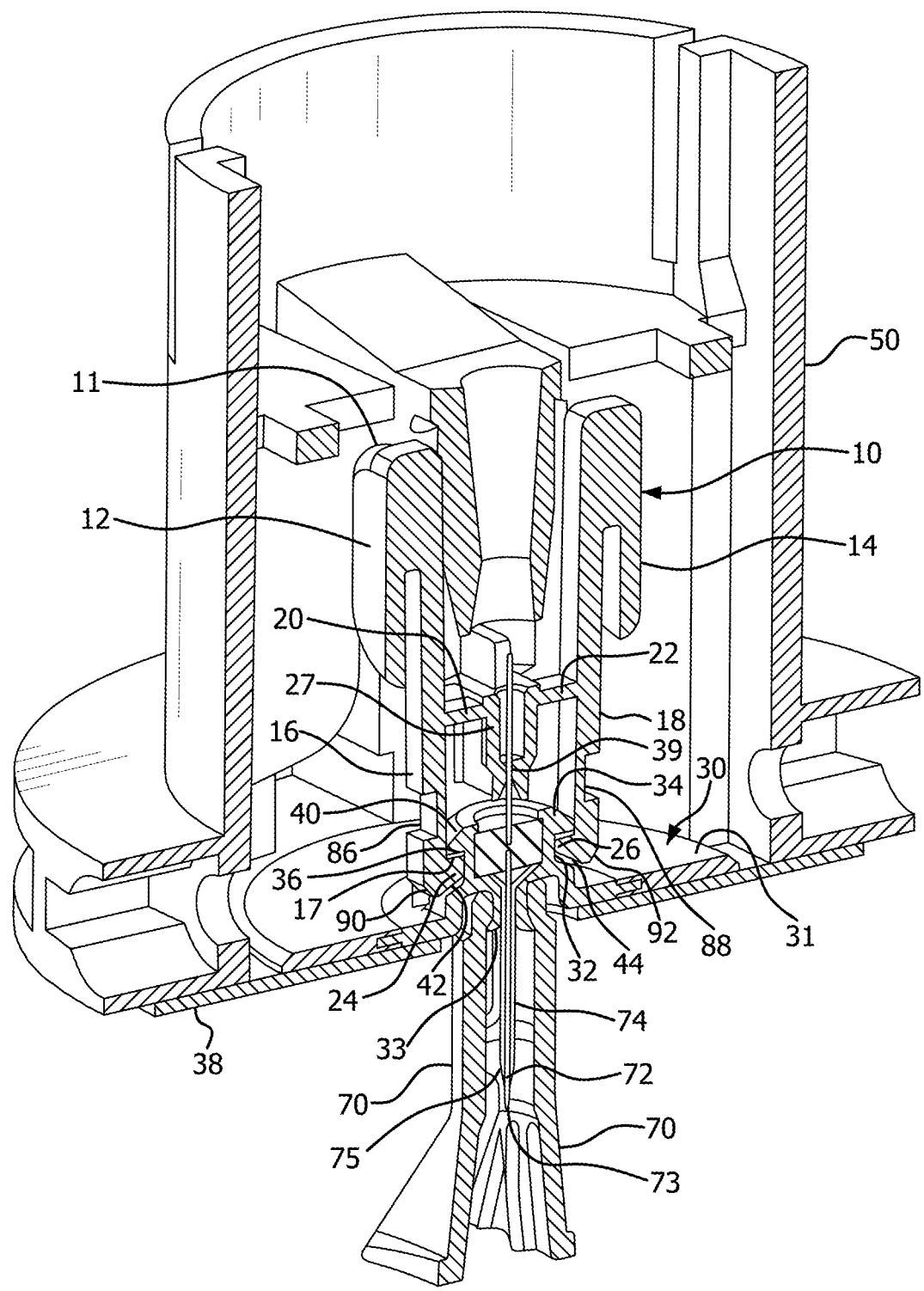
FIG. 1A is perspective a cross-sectional view of an insertor for a needle hub for an introducer needle, an medicament device base, an adhesive pad, a needle cover, and an insertion device in accordance with an embodiment of the present invention

Reference will now be made in detail to embodiments of the present invention, which are illustrated in the accompanying drawings, wherein like reference numerals refer to like elements throughout. The embodiments described herein exemplify, but do not limit, the present invention by referring to the drawings.

The embodiments are not intended to be mutually exclusive so that the features of one embodiment can be combined with other embodiments as long as they do not contradict each other.

It will be understood by one skilled in the art that this disclosure is not limited in its application to the details of construction and the arrangement of components set forth in the following description or illustrated in the drawings. The embodiments herein are capable of other embodiments, and capable of being practiced or carried out in various ways. Phraseology and terminology used herein is for the purpose of description and should not be regarded as limiting. The use of "including," "comprising," or "having" and variations thereof herein is meant to encompass the items listed thereafter and equivalents thereof as well as additional items.

Unless limited otherwise, the terms "connected," "coupled," and "mounted," and variations thereof herein are used broadly and encompass direct and indirect connections, couplings, and mountings. In addition, the terms "connected" and "coupled"" and variations thereof are not restricted to physical or mechanical connections or couplings. Further, terms such as "up," "down," "bottom," "top," "front," "rear," "upper," "lower," "upwardly," "downwardly," and other orientational descriptors are intended to facilitate the description of the exemplary embodiments of the present invention, and are not intended to limit the structure of the exemplary embodiments of the present invention to any particular position or orientation. Terms of degree, such as "substantially" or "approximately" are understood by those skilled in the art to refer to reasonable ranges around and including the given value and ranges outside the given value, for example, general tolerances associated with manufacturing, assembly, and use of the embodiments. The term "substantially" when referring to a structure or characteristic includes the characteristic that is mostly or entirely.

Figure 1B:
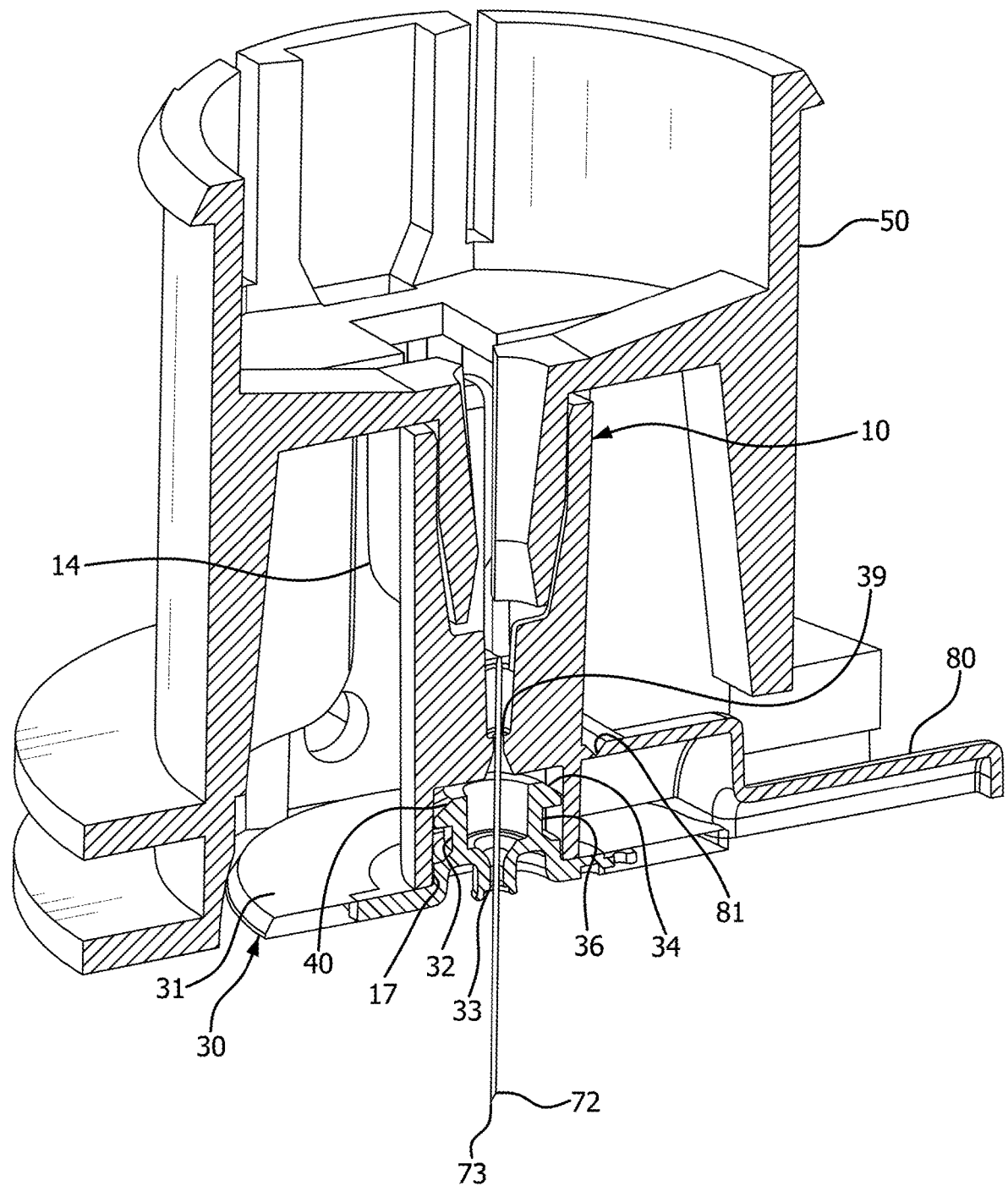
FIG. 1B is a perspective cross-sectional view of the insertor for the needle hub, the medicament device base, and the insertion device of FIG. 1A, with the perspective and cross-section rotated 90° relative to FIG. 1A.

FIGS. 1A and 1B illustrate an exemplary embodiment of a needle hub 10 of the present invention engaged with an medicament device base 30, such as an infusion set base. The inventive needle hub 10 is mounted in an insertion device 50 and a needle cover 70 protects an introducer needle 72. The medicament device base 30 is attached to an adhesive patch or pad 38 having an adhesive backing, which is used to secure the medicament device base 30 to a user's skin. Preferably, a removable adhesive liner protects the adhesive backing. FIG. 1 illustrates a state in which the needle hub 10 and medicament device base 30 are ready to facilitate insertion of a soft (flexible) catheter 74 and the introducer needle 72 into the user after removal of the needle cover 70 and the adhesive liner.

Figure 2A:
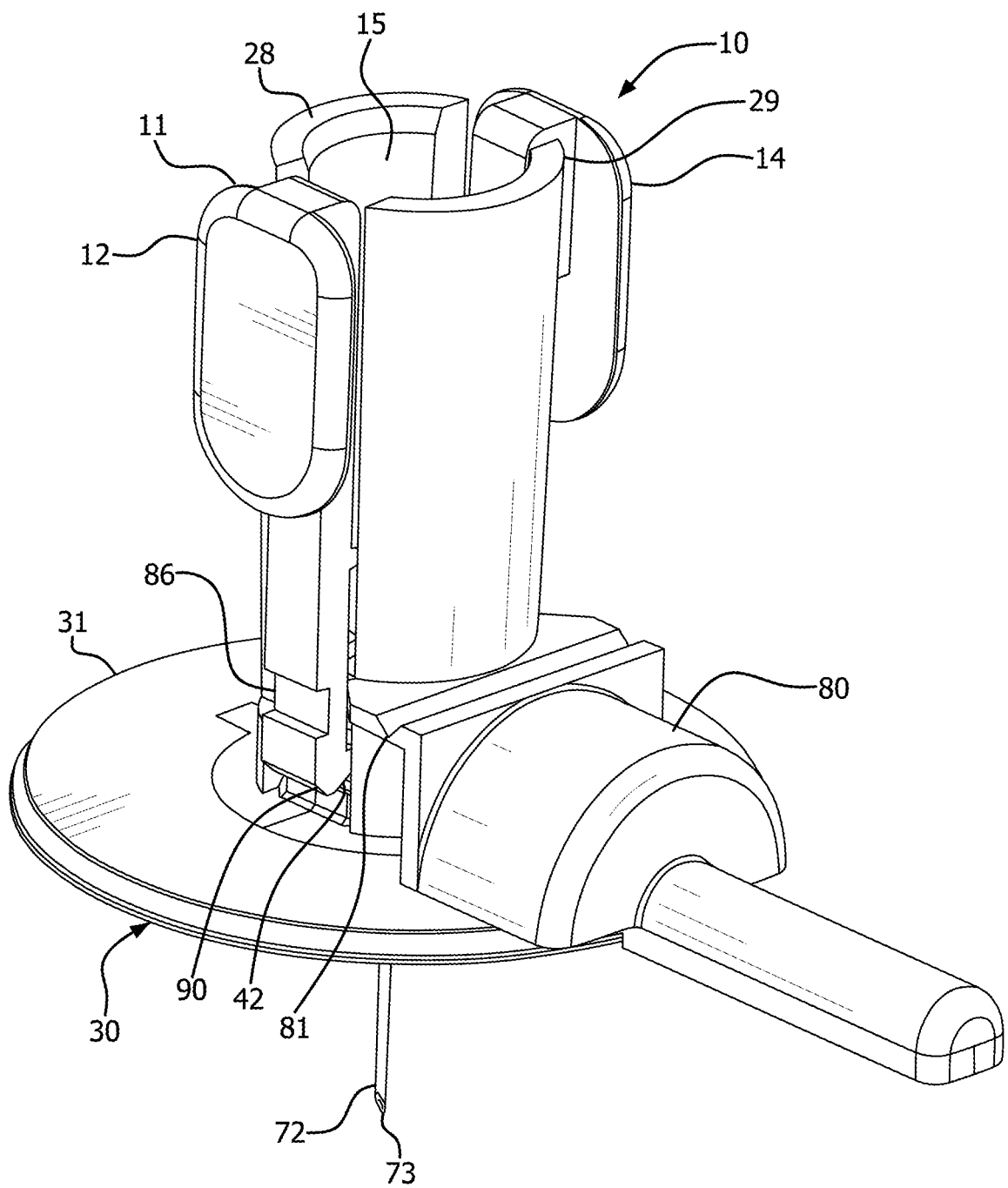
FIG. 2A is a perspective view.
Figure 2B:
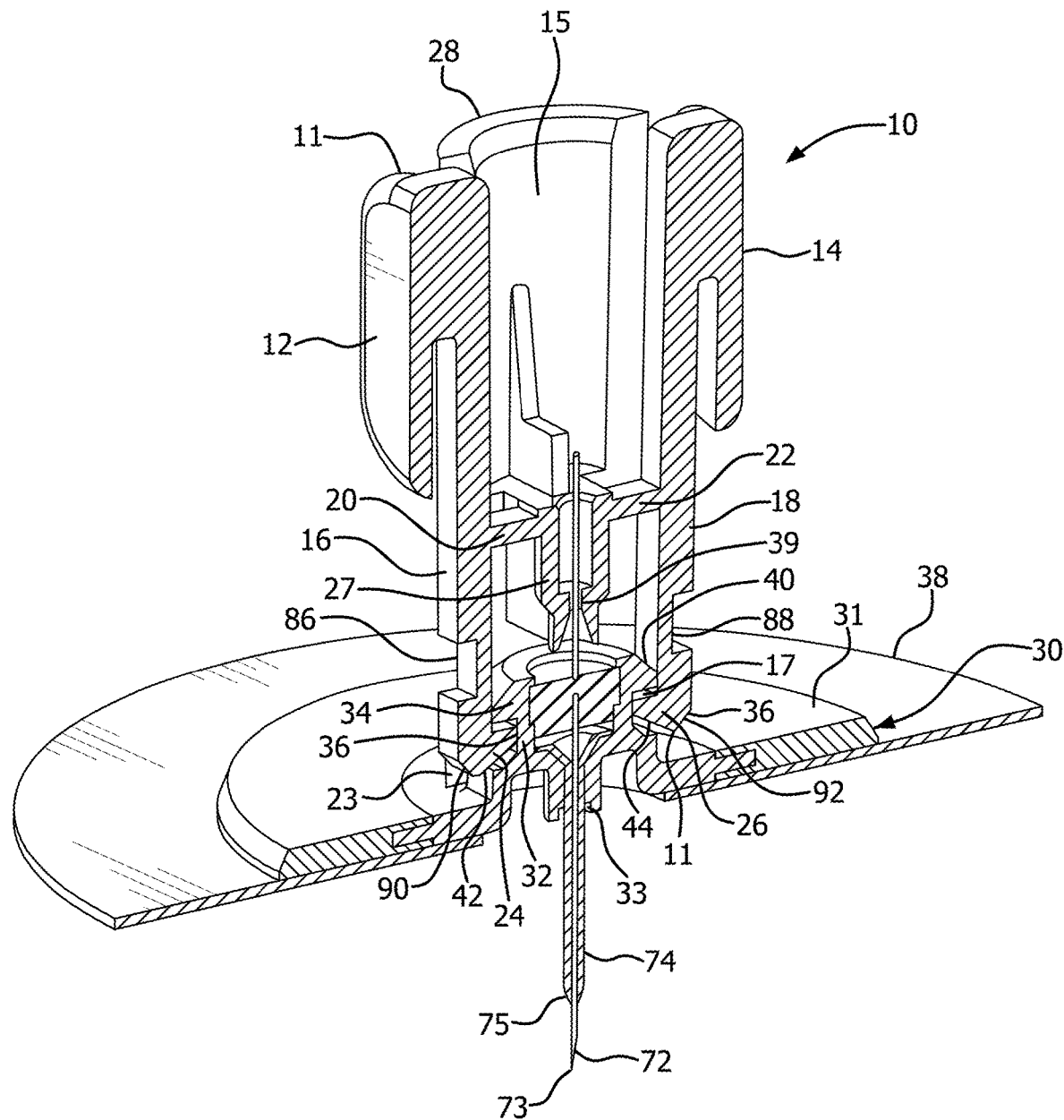
FIG. 2B is a perspective cross-sectional view.
Figure 2C:
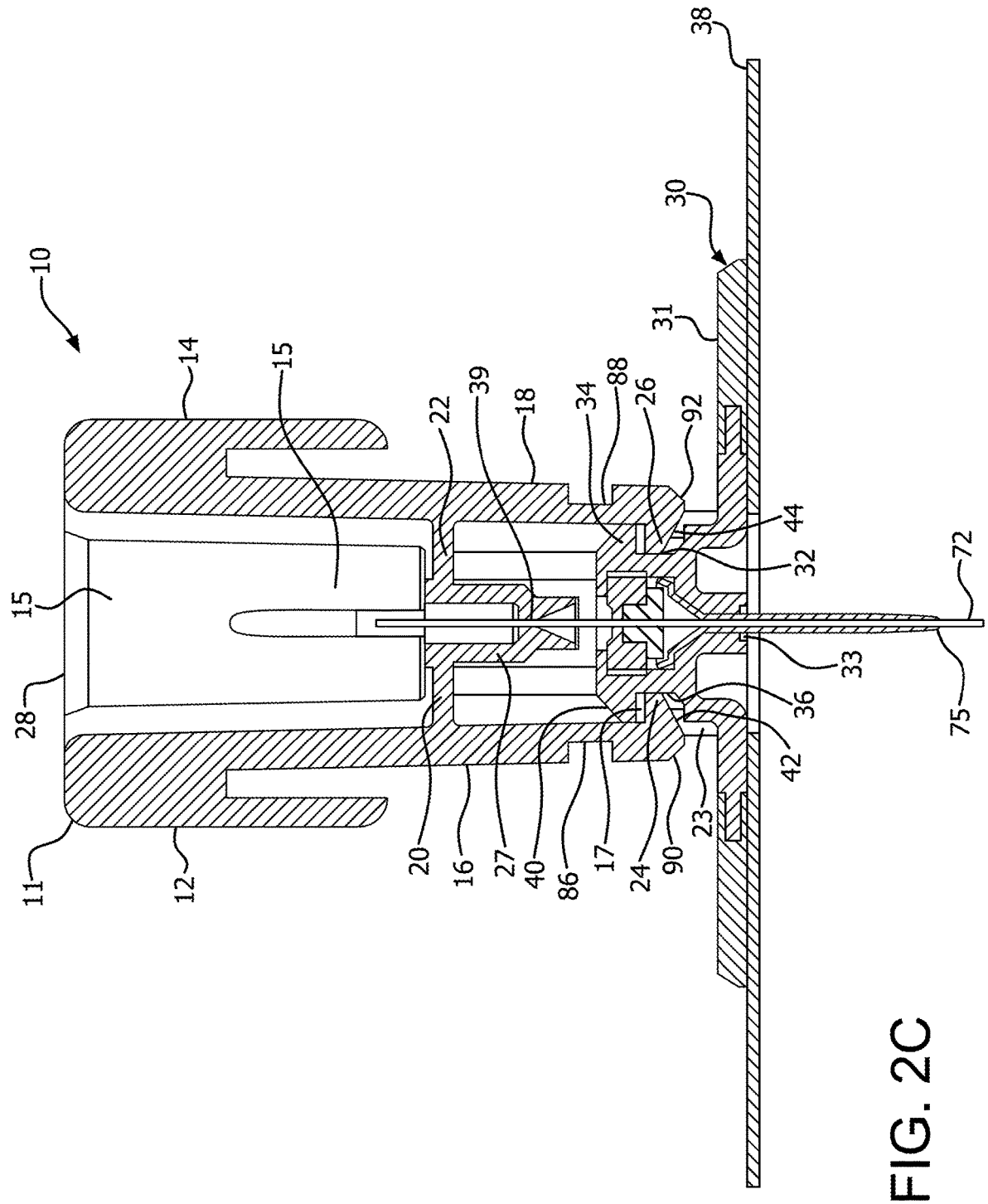
FIG. 2C is a perspective cross-sectional view with the perspective and cross-section rotated 90° relative to FIG. 2B.
Figure 2D:
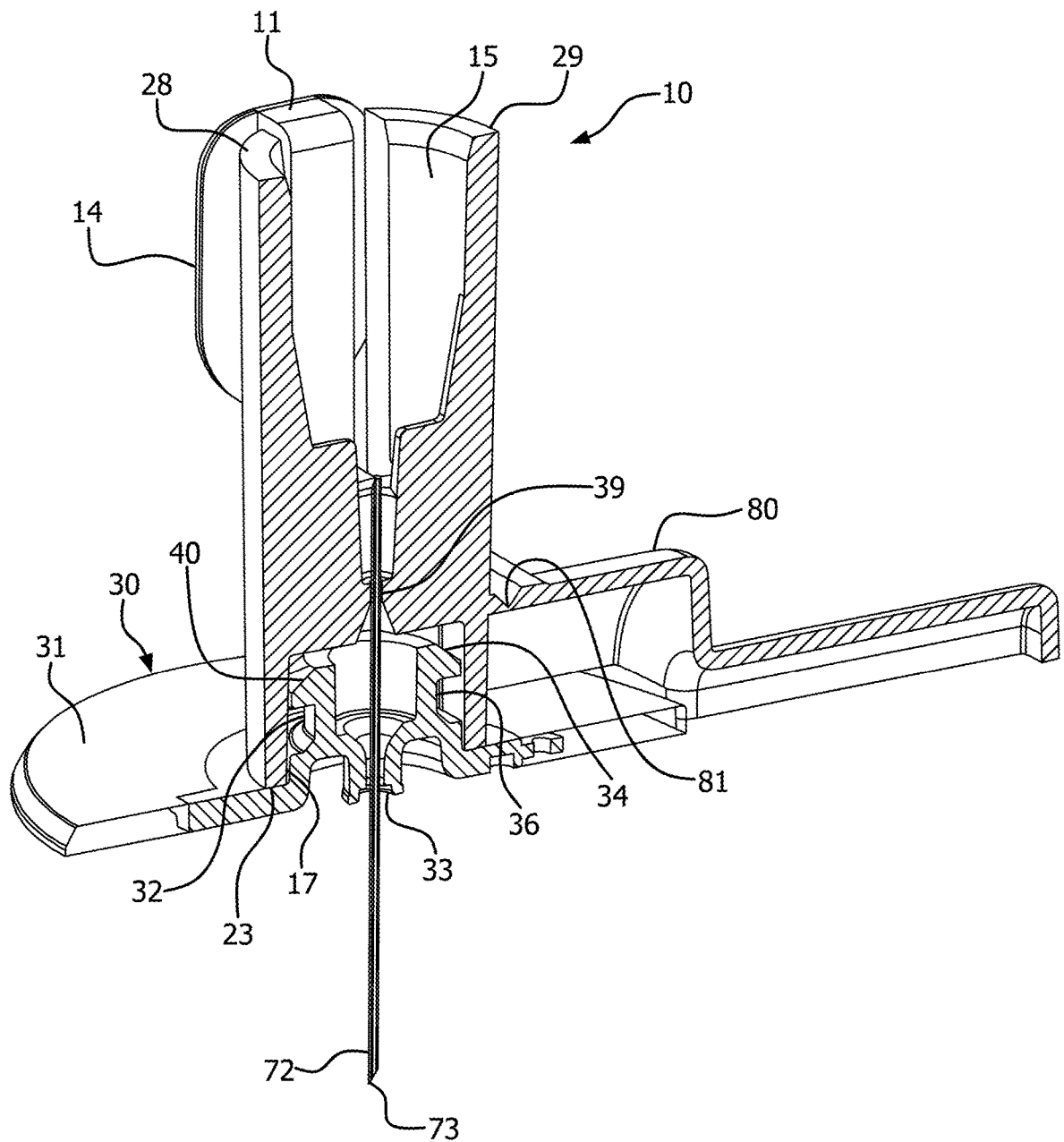
FIG. 2D is a perspective cross-sectional view with the perspective and cross-section rotated 90° relative to FIG. 2B, of the needle hub and the medicament device base of FIGS. 1A and 1B in a first operational state.

FIGS. 2A-2D illustrate the medicament device base 30 and the needle hub 10 in a first operational state. The needle hub 10 includes an interior cavity 15. In a preferred embodiment, a core mounting structure 27 includes an introducer needle cavity 39 and the introducer needle 72 is fixed to the introducer needle cavity 39 of the core mounting structure 27 by, for example, friction fit, adhesive, or a combination thereof. The introducer needle 72 is fixed against axial movement relative to the needle hub 10. As illustrated in FIGS. 2B-2D, the introducer needle cavity 39 is in coaxial alignment with the interior cavity 15. In addition to employing the introducer 50 for insertion the needle hub 10 itself can be used to insert the introducer needle 72 and the catheter 74 into the user. The introducer needle 72 is preferably a hollow stainless steel needle with a sharp beveled tip 73 at a distal end of the introducer needle 72.

Figure 3:
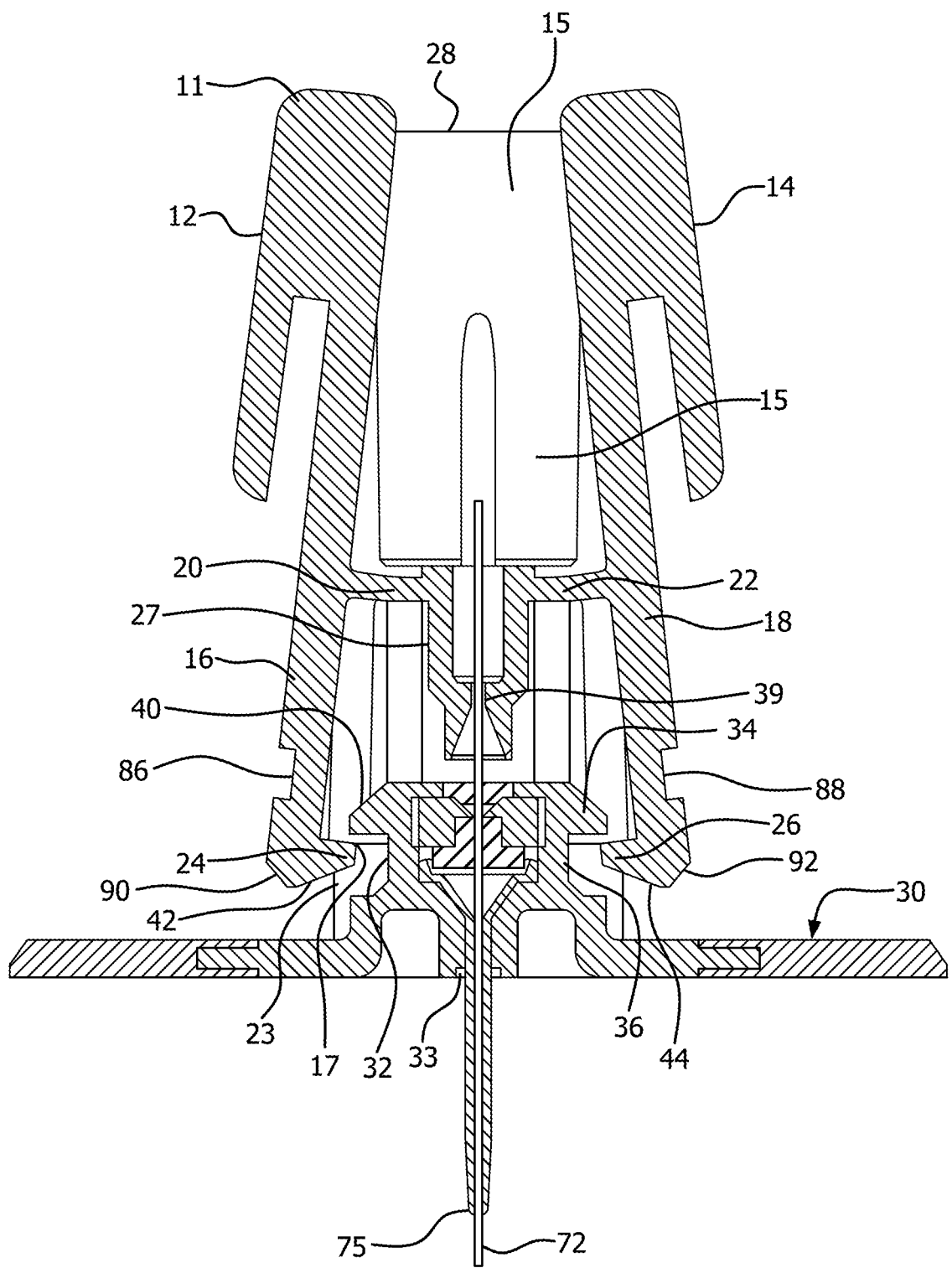
FIG. 3 is a cross-sectional view of the needle hub and the medicament device base of FIGS. 1A and 1B in a second operational state.

FIGS. 2A-6B further illustrate features of the needle hub 10. As shown, the needle hub 10 remains engaged with the medicament device base 30 after being removed from the insertion device 50. The core mounting structure 27 located in the interior cavity 15 is connected to first and second levers 16, 18 via needle hub latch hinges 20, 22. Each actuation lever 16, 18 includes a needle hub latch 24, 26 disposed at a distal end thereof to engage the needle hub 10 with the medicament device base 30 (see FIGS. 2 and 3). Additionally, each actuation lever 16, 18 includes an actuation button 12, 14 disposed at a proximal end thereof. Actuation levers 16, 18 are cantilevered longitudinally at central portions thereof from the core mounting structure 27. A first panel 28 and a second panel 29 (the latter shown in FIG. 2A) of the needle hub 10 are also connected to the core mounting structure 27. As shown in FIGS. 2 and 3, a distal end 23 of the first panel 28 extends further distally than first and second needle hub latches 24, 26 to engage an upper surface 31 of the medicament device base 30. This engagement promotes stability. Preferably, the distal end of the second panel 29 extends similarly.

Features of the needle hub 10 in a first state (prior to a user depressing the first and second actuation buttons 12, 14 and removing the needle hub 10 from the medicament device base 30) are illustrated in FIGS. 2A-2D. As shown, the medicament device base 30 includes a columnar post 32 surrounding an internal cavity 33. A head 34 is disposed at a proximal end of the columnar post 32. The head 34 may be configured in a mushroom-shape. According to one embodiment, the catheter 74 is fixedly connected to the internal cavity 33 of the columnar post 32. The introducer needle 72 can be removably disposed within the catheter 74 with the lie distance (distance between the catheter tip 75 and the sharp beveled tip 73 maintained by the needle hub 10 engaging the medicament device base 30 by, for example, the distal ends of the panels 28, 29 engaging the upper surface 31 of the medicament device base 30 (see, FIG. 2D).

As previously stated, the actuation buttons 12, 14 include actuation levers 16, 18 connected to the core mounting structure 27 via needle hub latch hinges 20, 22. Each of the actuation levers 16, 18 includes a needle hub latch 24, 26 disposed at a distal end thereof and can removably engage the undercut 36 formed by the columnar post 32 and head 34 on the medicament device base 30. When the actuation buttons 12, 14 are in a first, non-actuated state, the needle hub latches 24, 26 engage with the undercut 36 of the medicament device base 30 and the distal ends of the first and second panels 28, 29 sit on the upper surface 31 of the medicament device base 30 (see FIGS. 2B-2D). As shown, the head 34 extends into a distal opening 17 of the needle hub 10.

FIG. 3 illustrates the needle hub 10 in a second state, in which the user depresses the actuation buttons 12, 14. Preferably, the actuation buttons 12, 14 flex inward at a proximal end 11 of the needle hub 10 through openings between the first and second panels 28, 29 when a user depresses the actuation buttons 12, 14. The actuation levers 16, 18 pivot at needle hub latch hinges 20, 22 causing the needle hub latches 24, 26 to flex radially outward away from the undercut 36 on the medicament device base 30. As shown in FIG. 4, when the actuation buttons 12, 14 are in the second state and the needle hub latches 24, 26 are disengaged from the undercut 36 of the medicament device base 30, the first and second panels 28, 29 remain disposed on an upper surface 31 of the medicament device base 30.

As further shown in FIG. 3, the head 34 has a sloped head surface 40, and the actuation levers 16, 18 have inwardly ramped surfaces 42, 44 at distal cantilevered ends thereof. This allows the head 34 and medicament device base 30 attached to the head 34 to be inserted into the needle hub 10, as when the sloped head surface 40 engages with the distal free end inwardly ramped surfaces 42, 44, the actuation levers 16, 18 pivot at needle hub latch hinges 20, 22, causing the needle hub latches 24, 26 to flex radially outward, allowing the head 34 to move upward as the distal free end opens up, until the needle hub latches 24, 26 engage the undercut 36 and lock the needle hub 10 and the head 34 together.

Figure 4A:
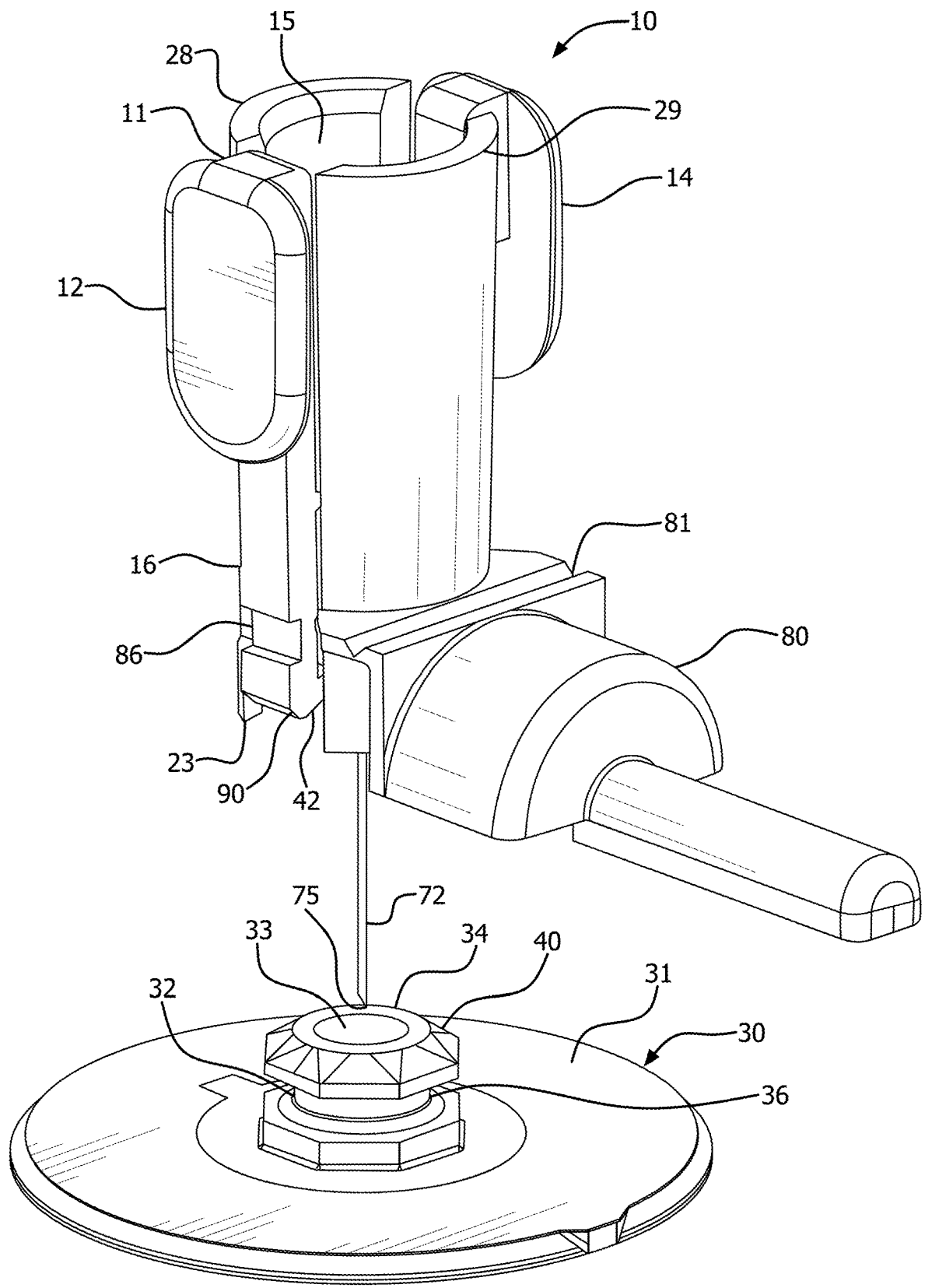
FIG. 4A is a is a perspective view and FIG. 4B is a perspective cross-sectional view, of the needle hub of FIGS. 1A and 1B in a fully deployed state and removed from the medicament device base of FIG. 1, with FIG. 4A further showing a needle tip shield in a first position.
Figure 4B:
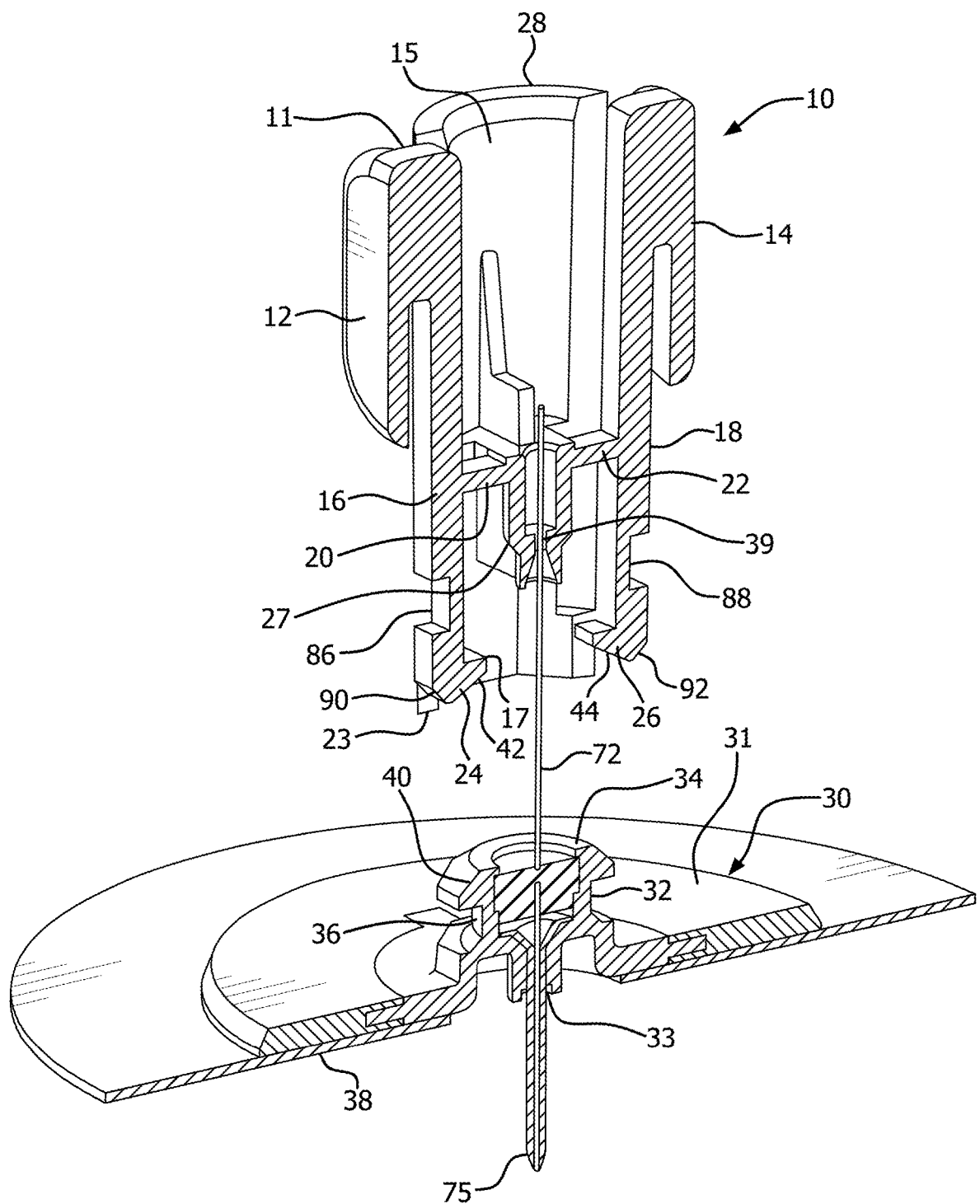
Figure 5A:
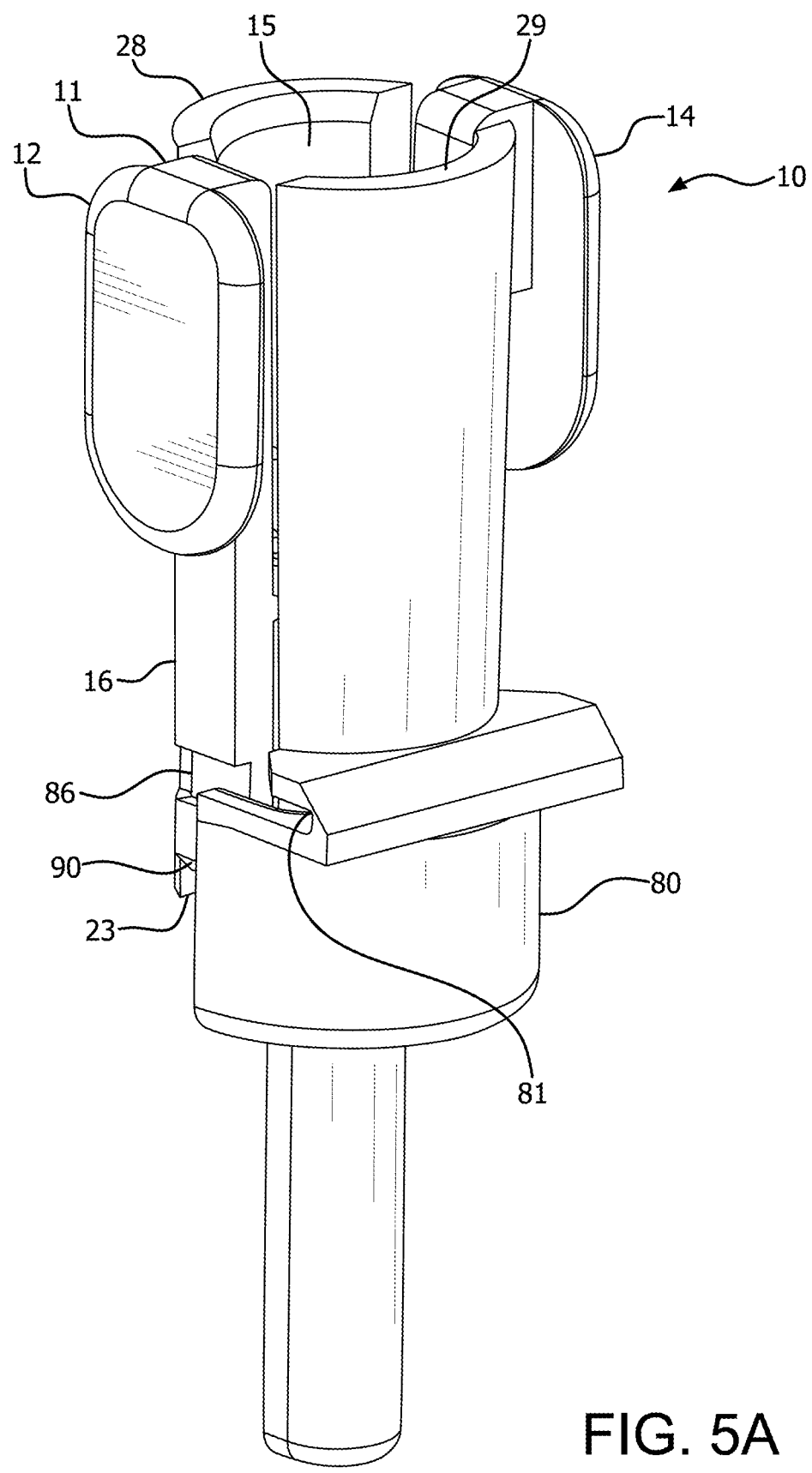
FIG. 5A is a perspective view.
Figure 5B:
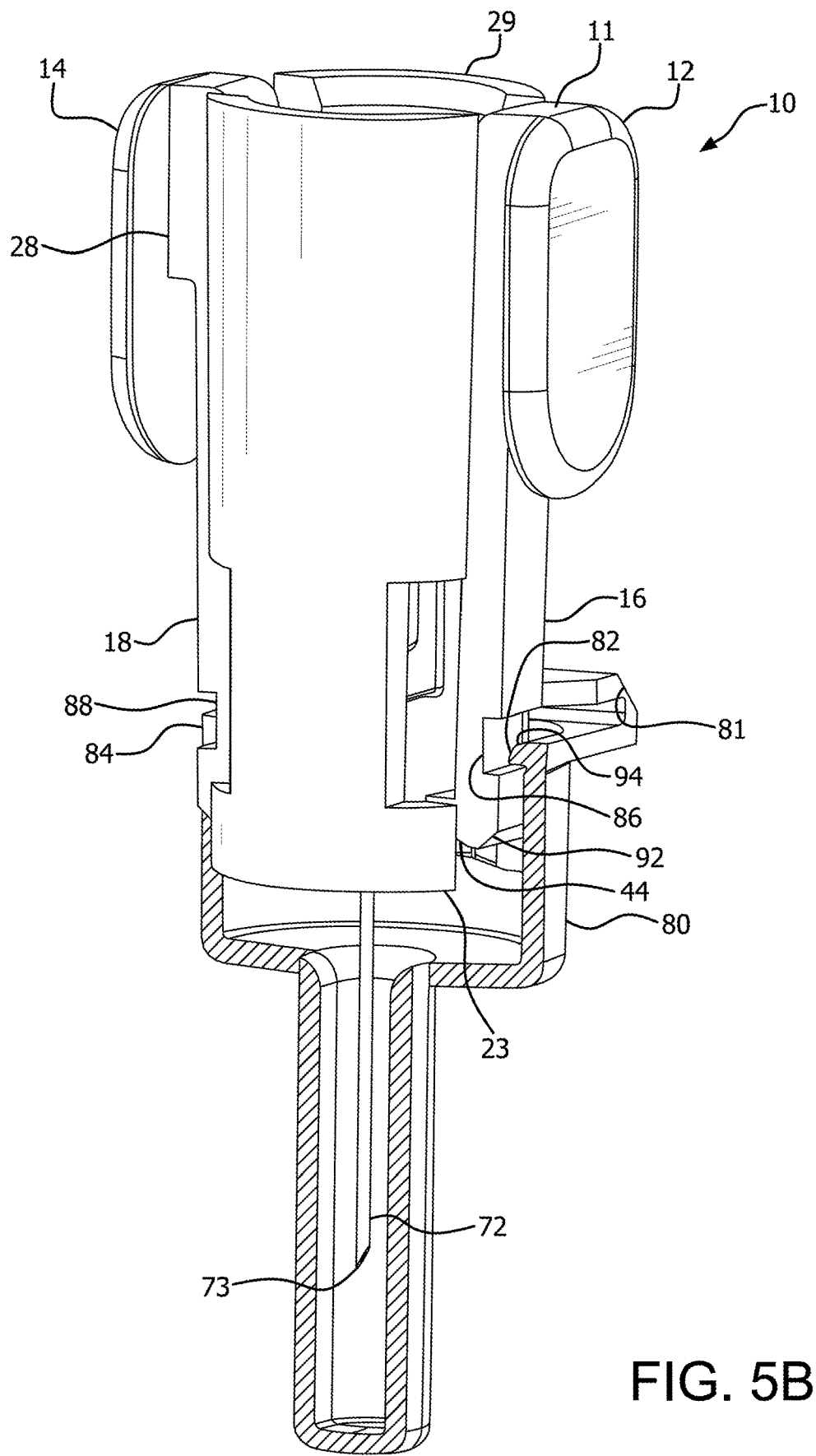
FIG. 5B is a perspective view rotated 90° relative to FIG. 5A.
Figure 5C:
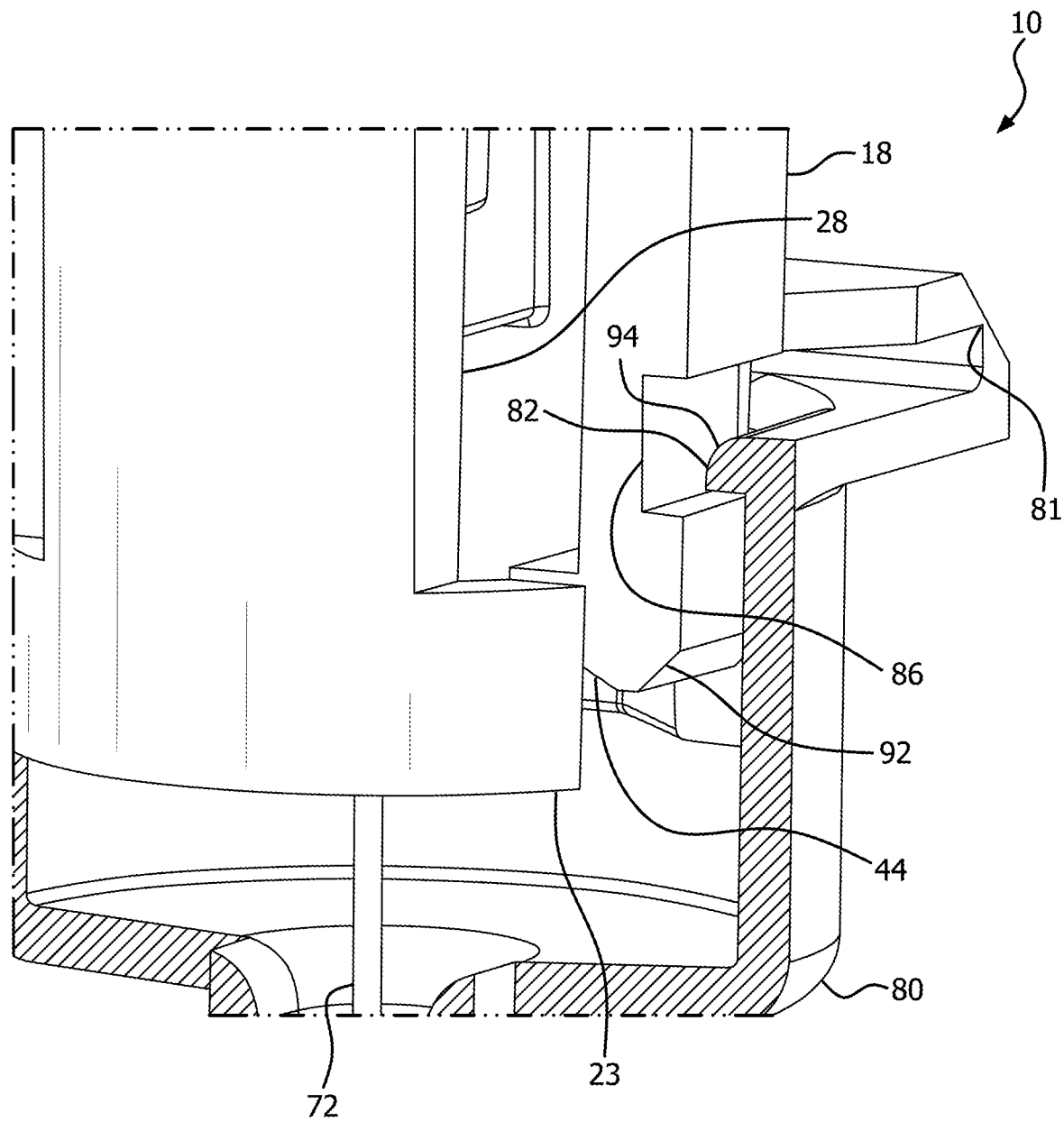
FIG. 5C is a partial perspective view of FIG. 5B, of the needle hub of FIGS. 1A and 1B in a second position.

FIGS. 4A and 4B illustrate a state in which the needle hub 10 is in the process of being removed from the medicament device base 30, and the first and second panels 28, 29 are removed from the upper surface 31 of the medicament device base 30. The user maintains pressure on the actuation buttons 12, 14 while lifting the needle hub 10 relative to the medicament device base 30, at least until needle hub latches 24, 26 clear the head 34. After the needle hub 10 is removed and the user releases pressure on the actuation buttons 12, 14, the needle hub latch hinges 20, 22 also relax and the needle hub latches 24, 26 return to the unflexed position of the first state. As shown in FIG. 4A, the user can now complete withdrawal of the introducer needle 72 from the catheter 74 of the medicament device base 30.

Referring back to FIG. 1A, in one embodiment, the needle hub 10 includes a needle cover 70 where the needle cover 70 engages with the medicament device base 30 in an initial state. According to one embodiment, when the needle hub 10 is removed from the medicament device base 30, the needle cover 70 can cover the introducer needle 72 mounted to the needle hub 10 to prevent a needle stick injury. For example, in some alternative embodiments, the needle hub latches 24, 26 can engage the needle cover 70 to retain the needle cover 70 on the needle hub 10, e.g., via recesses in the needle cover's exterior. Alternatively, or in addition, the distal end of the core mounting structure 27 can be configured to mate with the proximal end of the needle cover 70, similar to the way the proximal end of the needle cover 70 mates with the medicament device base 30.

Figure 6A:
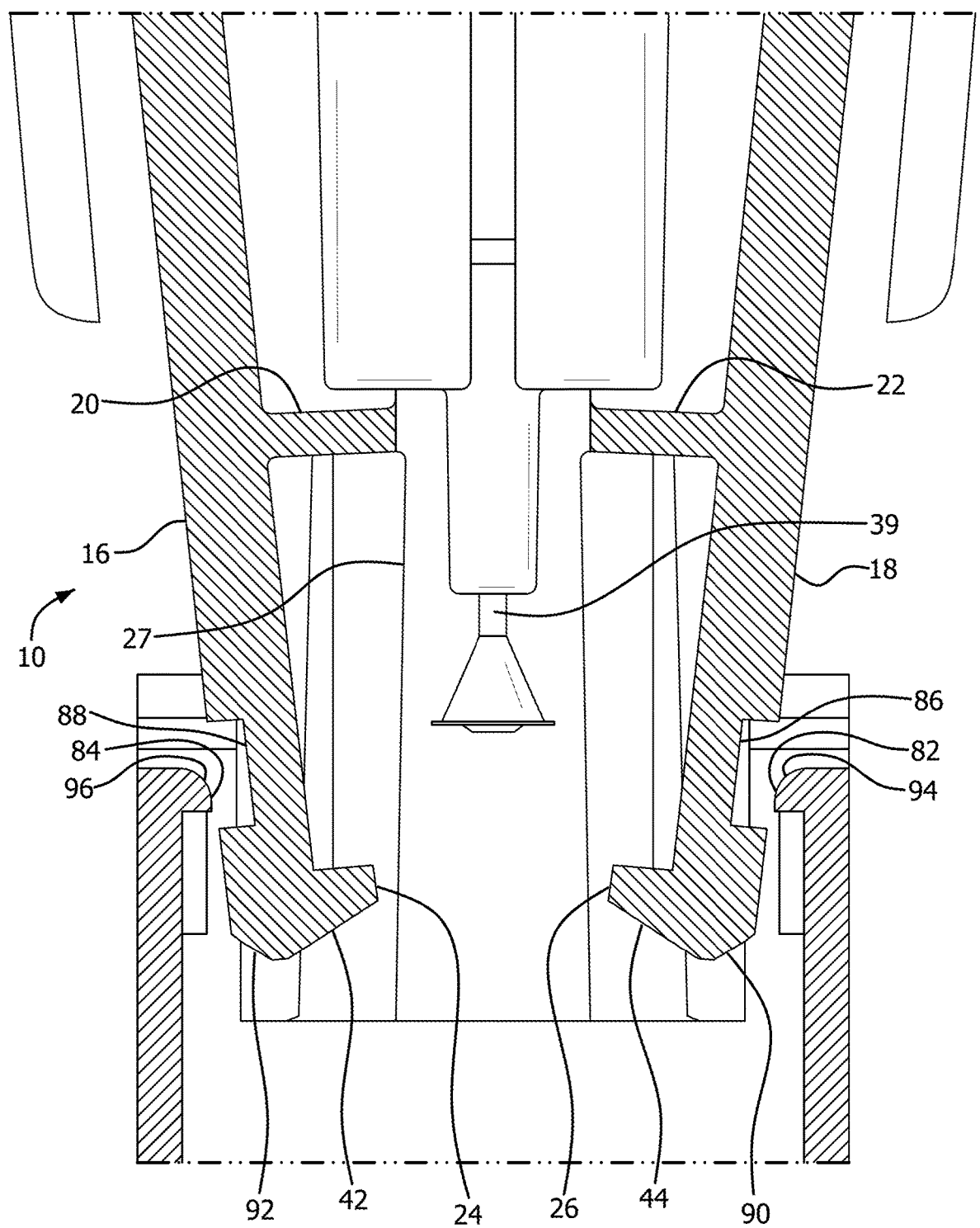
FIG. 6A is a partial view of the needle hub of FIGS. 1A and 1B in the second position.
Figure 6B:
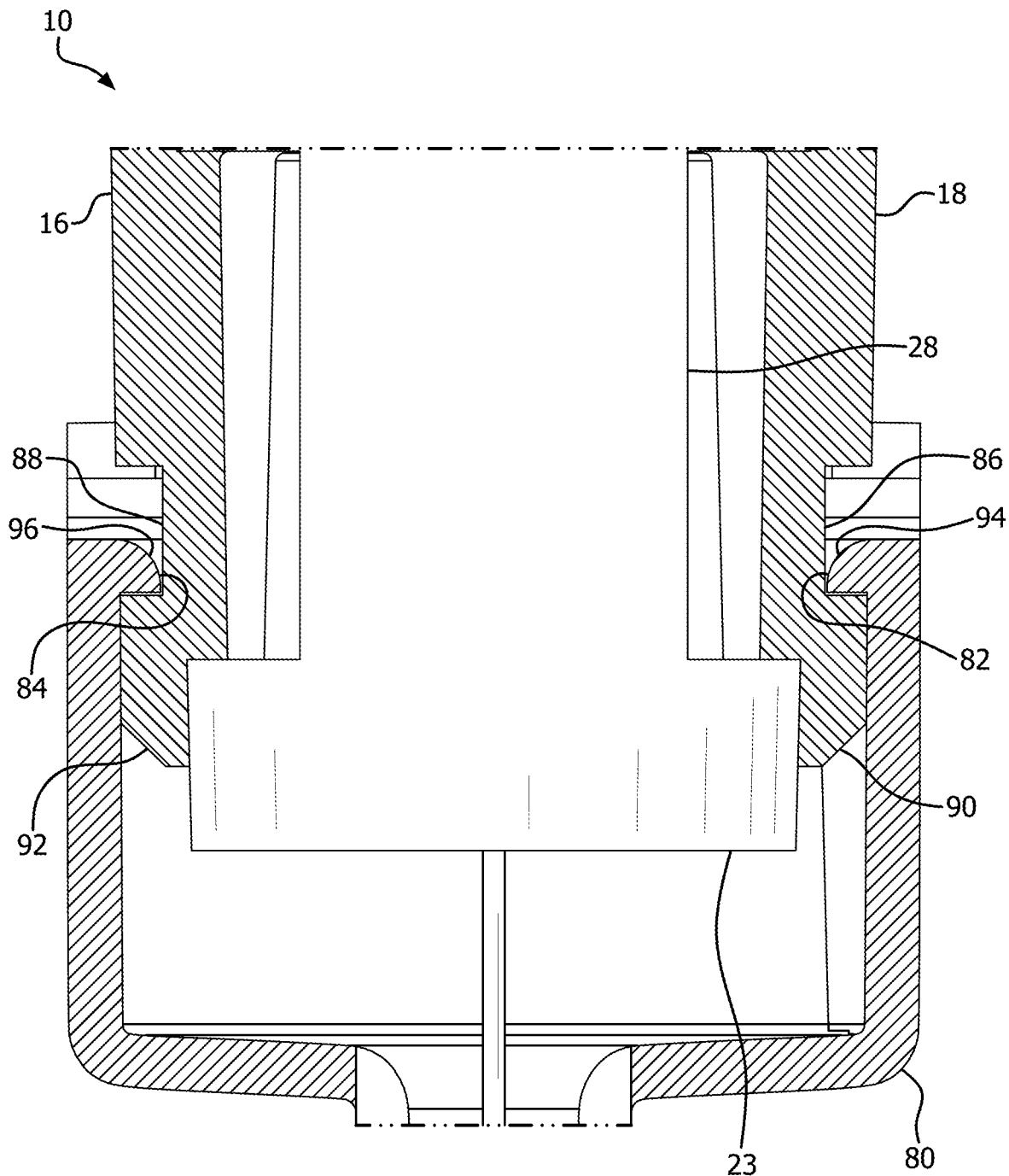
FIG. 6B is a partial cross-sectional view of the needle hub of FIGS. 1A and 1B showing the needle tip shield between the first position and a second position.

Another mechanism for preventing needle stick is shown in FIGS. 1B, 2A, 4A, 4C, 5A-5C, and 6A-6B. In particular, the needle hub 10 includes a needle tip shield 80 rotatably connected to the second panel 29. The needle tip shield 80 is rotatable at a hinge 81 from a first position in which the sharp beveled tip 73 of the needle 72 is exposed, shown best in FIG. 4A, to a second position shielding the sharp beveled tip 73 of the needle 72, shown in FIGS. 5A-5C and 6B. FIG. 6A shows an intermediate state in which the needle tip shield 80 is in the process of rotating between the first position and the second position. The needle tip shield 80 includes a pair of needle tip shield latches 82, 84 and the actuation levers 16, 18 each include exterior grooves 86, 88 or detents at respective distal free ends that engage the needle tip shield latches 82, 84 upon the needle tip shield 80 reaching the second position and lock the needle tip shield 80 in the second position.

As best seen in FIG. 6A, the movement of the needle tip shield 80 from the first position to the second position is aided by distal free end outwardly ramped surfaces 90, 92 and needle tip latch ramped surfaces 94, 96, such that the distal free end outwardly ramped surfaces 90, 92 engage the needle tip shield latch ramped surface 94, 96 as the needle tip shield 80 rotates from the first position to the second position, causing the distal free ends of the actuation levers 16, 18 to pivot inward and the proximal free ends of the actuation levers 16, 18 to pivot outward.

Although only a few embodiments of the present invention have been shown and described, the present invention is not limited to the described embodiments. Instead, it will be appreciated by those skilled in the art that changes may be made to these embodiments without departing from the principles and spirit of the invention. Any of the embodiments and/or elements disclosed herein may be combined with one another to form various additional embodiments not specifically disclosed, as long as they do not contradict each other. It is particularly noted that those skilled in the art can readily combine the various technical aspects of the various elements of the various exemplary embodiments that have been described above in numerous other ways, all of which are considered to be within the scope of the invention, which is defined by the appended claims and their equivalents.

Various aspects of the multiple embodiments may be employed independently or in combinations thereof.

What is claimed is:

1. A needle hub, comprising:
   a core mounting structure;

a first panel and a second panel, each connected to the core mounting structure with an opening formed between the first panel and the second panel;

an introducer needle fixedly attached to the core mounting structure for insertion into a patient;

a first actuation lever disposed within the opening, cantilevered at a central portion of the first actuation lever from the core mounting structure, and having a first actuation button disposed at a proximal cantilevered end of the first actuation lever and a first needle hub latch disposed at a distal cantilever end of the first actuation lever; and a needle tip shield rotatably connected to one of the first panel or the second panel and rotatable by a user from a first position in which a distal end of the introducer needle is exposed to a second position shielding the distal end of the introducer needle when the distal cantilever end of the first actuation lever pivots inwardly.

2. The needle hub according to claim 1, wherein:

the first needle hub latch is disposed on an interior of the distal cantilever end of the first actuation lever;

the needle tip shield includes a needle tip shield latch; and an exterior of the distal cantilever end of the first actuation lever includes a feature configured to engage the needle tip shield latch upon the needle tip shield reaching the second position and lock the needle tip shield in the second position.

3. The needle hub according to claim 2, wherein the feature comprises a groove; and the feature moves inwardly when the needle tip shield moves between the first position and the second position.

4. The needle hub according to claim 2, wherein the feature comprises a detent.

5. The needle hub according to claim 2, wherein the needle tip shield latch or the distal cantilever end of the first actuation lever comprises a ramped surface, the ramped surface configured to engage the needle tip shield latch and the distal cantilever end of the first actuation lever as the needle tip shield rotates from the first position to the second position and cause the distal cantilever end of the first actuation lever to pivot inward and the proximal cantilevered end of the first actuation lever to pivot outward.

6. The needle hub according to claim 2, wherein each of the needle tip shield latch and the distal cantilever end of the first actuation lever comprises a ramped surface, the ramped surface of the needle tip shield latch and the ramped surface of the distal cantilever end of the first actuation lever being configured to engage each other as the needle tip shield rotates from the first position to the second position and cause the distal cantilever end to pivot inward and the proximal cantilevered end to pivot outward.

7. The needle hub according to claim 2, wherein the distal cantilever end of the first actuation lever comprises:

a radially inward ramped surface configured to engage a medical device; and a radially outward ramped surface configured to:

engage the needle tip shield latch as the needle tip shield rotates from the first position to the second position: and upon engagement with the needle tip shield latch, cause the distal cantilever end of the first actuation lever to pivot inward and cause the proximal cantilevered end of the first actuation lever to pivot outward.

8. The needle hub according to claim 1, wherein the first panel and the second panel extend further distally than the first needle hub latch of the first actuation lever and are configured to promote stability of the needle hub during attachment of the needle hub to a medical device.

9. The needle hub according to claim 1, further comprising a second actuation lever cantilevered at a central portion thereof from the core mounting structure and having a second actuation button disposed at a proximal cantilevered end of the second actuation lever and a second needle hub latch disposed at a distal cantilever end of the second actuation lever, wherein the first actuation lever and second actuation lever releasably couple the needle hub to a medical device.

10. A combination, comprising:

the needle hub according to claim 1; and a medicament device base including:

a columnar post extending from the medicament device base;

a head disposed at a proximal end of the columnar post; and an undercut formed by the columnar post and the head, wherein the first actuation lever engages the undercut of the medicament device base to removably engage the needle hub with the medicament device base;

wherein the first needle hub latch engages the undercut to secure the needle hub and the medicament device base together; and wherein the first actuation button is configured to pivot radially inward, thereby causing the distal cantilever end of the first actuation lever to pivot outward and disengage from the undercut.

11. The combination according to claim 10, wherein:

the first needle hub latch is disposed on an interior of the distal cantilever end of the first actuation lever;

the needle tip shield includes a needle tip shield latch; and an exterior of the distal cantilever end of the first actuation lever includes a feature to engage the needle tip shield latch upon the needle tip shield reaching the second position and lock the needle tip shield in the second position.

12. The combination according to claim 11, wherein the distal cantilever end of the first actuation lever comprises:

a radially inward ramped surface configured to:

engage the head of the medicament device base; and upon engagement with the head of the medicament device base, cause the distal cantilever end of the first actuation lever to pivot outward and cause the proximal cantilevered end of the first actuation lever to pivot inward; and a radially outward ramped surface configured to:

engage the needle tip shield latch as the needle tip shield rotates from the first position to the second position; and upon engagement with the needle tip shield latch, cause the distal cantilever end of the first actuation lever to pivot inward and cause the proximal cantilevered end of the first actuation lever to pivot outward.

13. A needle hub, comprising:

a core mounting structure connected to an introducer needle;

a pair of actuation levers pivotally connected to the core mounting structure, each of the pair of actuation levers comprising an actuation button disposed at a proximal cantilevered end and a needle hub latch disposed at a distal cantilevered end;

a first panel connected to the core mounting structure and disposed adjacent to the pair of actuation levers; and a needle tip shield rotatably connected to the first panel, and rotatable by a user from a first position in which a distal end of the introducer needle is exposed to a second position shielding the distal end of the introducer needle when the distal cantilevered end of at least one of the pair of actuation levers pivots inwardly.

14. The needle hub according to claim 13, wherein:
the needle hub latches of each of the pair of actuation levers are disposed on respective interiors of the distal cantilevered ends of the pair of actuation levers;
the needle tip shield includes one or more needle tip shield latches; and
respective exteriors of the distal cantilevered ends of each of the pair of actuation levers includes a feature to engage at least one of the one or more needle tip shield latches upon the needle tip shield reaching the second position and to lock the needle tip shield in the second position, the feature moves inwardly when the needle tip shield moves between the first position and the second position.

15. The needle hub according to claim 14, wherein the needle tip shield latches or the distal cantilevered ends of each of the pair of actuation levers comprises a ramped surface, the ramped surfaces are configured to engage the one or more needle tip shield latches and the distal cantilevered ends of each of the pair of actuation levers as the needle tip shield rotates from the first position to the second position and cause the distal cantilevered ends of each of the pair of actuation levers to pivot inward and proximal cantilevered ends of each of the pair of actuation levers to pivot outward.

16. The needle hub according to claim 14, wherein each of the one or more needle tip shield latches and the distal cantilevered ends of each of the pair of actuation levers comprises a ramped surface, the ramped surface of the one or more needle tip shield latches and the ramped surface of the distal cantilevered ends of each of the pair of actuation levers being configured to engage each other as the needle tip shield rotates from the first position to the second position and cause the distal cantilevered ends of each of the pair of actuation levers to pivot inward and proximal cantilevered ends of each of the pair of actuation levers to pivot outward.

17. The needle hub according to claim 14, wherein the distal cantilevered ends of each of the pair of actuation levers comprises:
a radially inward ramped surface configured to engage a medical device; and
a radially outward ramped surface configured to:
engage at least one of the one or more needle tip shield latches as the needle tip shield rotates from the first position to the second position: and
upon engagement with at least one of the one or more needle tip shield latches, cause the distal cantilevered ends of each of the pair of actuation levers to pivot inward and cause proximal cantilevered ends of each of the pair of actuation levers to pivot outward.

18. The needle hub according to claim 13, further comprising a second panel opposed to the first panel and connected to the core mounting structure; and
wherein the first panel and the second panel extend further distally than the needle hub latches of each of the pair of actuation levers and are configured to promote stability of the needle hub during attachment of the needle hub to a medical device.

19. A combination, comprising:
the needle hub according to claim 13; and
a medicament device base including:
a columnar post extending from the medicament device base;
a head disposed at a proximal end of the columnar post; and
an undercut formed by the columnar post and the head, wherein the pair of actuation levers engage the undercut of the medicament device base to removably engage the needle hub with the medicament device base;
wherein the needle hub latches engage the undercut to secure the needle hub and the medicament device base together; and
wherein the actuation buttons of each of the pair of actuation levers are configured to pivot radially inward, thereby causing the distal cantilevered ends of the pair of actuation levers to pivot outward and disengage from the undercut.

20. A method, comprising:
inwardly pinching a proximal cantilevered end of a pivotally connected actuation lever of a needle hub having an introducer needle, to outwardly displace a needle hub latch disposed on a distal cantilevered end of the pivotally connected actuation lever and unlatch the needle hub from a medicament device base;
proximally displacing the needle hub to remove the introducer needle from the medicament device base; and
folding a rotatably connected needle tip shield of the needle hub from a first position in which a distal end of the introducer needle is exposed to a second position shielding the distal end of the introducer needle, and during the folding, causing the rotatably connected needle tip shield to contact and pivot the distal cantilevered end of the pivotally connected actuation lever inwardly.

* * * * *